United States Patent [19]

Mann et al.

[11] 4,169,778

[45] Oct. 2, 1979

[54] HEATED SOLID ELECTROLYTE OXYGEN SENSOR

[75] Inventors: Gamdur S. Mann; Michael P. Murphy, both of Flint; David R. Fredericks, Grand Blanc; Kenneth R. Deming, Flint, all of Mich.

[73] Assignee: General Motors Corporation, Detroit, Mich.

[21] Appl. No.: 961,137

[22] Filed: Nov. 16, 1978

[51] Int. Cl.² .................................................. G01N 27/58
[52] U.S. Cl. .................................................. 204/195 S
[58] Field of Search .............. 204/195 S, 1 S; 60/276; 123/119 E, 119 EC; 324/29

[56] References Cited

U.S. PATENT DOCUMENTS

| | | | |
|---|---|---|---|
| 3,357,910 | 12/1967 | Shiller | 204/195 S |
| 3,546,086 | 12/1970 | Sayles | 204/195 S |
| 3,616,274 | 10/1971 | Eddy | 204/1 T |
| 3,815,560 | 6/1974 | Wahl et al. | 123/117 R |
| 3,844,920 | 10/1974 | Burgett et al. | 204/195 S |
| 4,129,099 | 12/1978 | Howarth | 123/32 EE |

*Primary Examiner*—G. L. Kaplan
*Attorney, Agent, or Firm*—Robert J. Wallace

[57] ABSTRACT

A readily manufacturable heated solid electrolyte oxygen sensor having an elongated heater supported in subassembly with a tubular terminal for a reference electrode of the sensor. The heater is coaxial with the electrode terminal for predetermined disposition with respect to the sensor solid electrolyte member. The heater includes a rod coaxially in a ceramic tube and a resistance heating coil and crimped outer connector around the ceramic tube. Fused glass, directly bonded to the ceramic tube, supports the heater in the electrode terminal.

3 Claims, 3 Drawing Figures

HEATED SOLID ELECTROLYTE OXYGEN SENSOR

BACKGROUND OF THE INVENTION

This invention relates to a heated galvanic solid electrolyte oxygen sensor, and more particularly to improvements in a heater-reference electrode terminal subassembly for such a sensor.

Solid electrolyte galvanic oxygen sensors essentially include an oxygen ion conductive ceramic body with porous electrodes on opposite faces of the body. One electrode is exposed to a reference source of oxygen. The other electrode is exposed to a source whose oxygen content is to be measured. A difference in oxygen partial pressure at the electrodes produces a corresponding potential difference across the electrodes, which provides a sensor output voltage.

The output voltage of such sensors can be used as a measure of oxygen or unburned combustibles in exhaust gases from an internal combustion engine. This voltage can be used in both monitoring and controlling the engine combustion process, as disclosed in U.S. Pat. Nos. 3,616,274 Eddy, 3,844,920 Burgett et al. and U.S. Ser. No. 787,900 Howarth, filed Apr. 15, 1977, now U.S. Pat. No. 4,129,099, and assigned to the assignee of this invention. To obtain an appreciable output voltage, the sensor solid electrolyte is heated to an elevated temperature. Also, sensor output voltage varies with changes in temperature, especially at lower operating temperatures. Combustion gases can be used to heat the sensor to operating temperatures but such gases vary widely in temperature, particularly when from an internal combustion engine. Moreover, the combustion gases may cool significantly before contacting the sensor or may not heat the sensor fast enough on start up. Consequently, it has previously been proposed to supply supplementary heat for the sensor, and even include a resistance heater in the sensor itself. One such heated sensor construction is disclosed in the United States patent application Ser. No. 892,642, filed by Murphy et al. on Apr. 3, 1978 and entitled "Solid Electrolyte Oxygen Sensor with Electrically Isolated Heater." Murphy et al. disclose a sheathed heater insulatingly supported in subassembly with a tubular terminal for a reference electrode on the solid electrolyte of the sensor. A resistance heating coil is buried within a ceramic powder contained within the heater sheath. The heater is aligned with the electrode terminal. When the electrode terminal is aligned with the solid electrolyte body, the heater is inherently also aligned with it. A ceramic sleeve spaces the heater and electrode terminal and bonded to them in subassembly by a fused glass. This provides a rugged, reliable and readily manufacturable and readily assembled subassembly for a heated automobile exhaust gas oxygen sensor in which all terminals are coaxial, and the heater is electrically isolated from sensor terminals. in this way the aforementioned U.S. Ser. No. 892,642 presents an improvement on the heater-terminal subassembly concept claimed in the U.S. patent application Ser. No. 892,644 Murphy that was concurrently filed therewith and entitled "Heated Solid Electrolyte Oxygen Sensor."

We have now found how to improve the isolated heater-electrode terminal subassembly even further. We have found how to increase heating efficiency, reduce manufacturing costs, and even enhance bonding of the heater-terminal subassembly. Moreover, yields in manufacturing of the heater in this subassembly should be higher. The manufacturing and assembly techniques are more familiar, and do not require as much precision in performance.

OBJECTS AND SUMMARY OF THE INVENTION

It is an object of this invention to provide an improved, heated solid electrolyte oxygen sensor.

Another object of the invention is to provide an improved insulated heater-electrode terminal subassembly for a solid electrolyte oxygen sensor.

The invention comprehends a solid electrolyte galvanic oxygen sensor having a heater-electrode terminal subassembly readily assemblable with the electrolyte member and a surrounding housing. The heater is insulatingly supported on the terminal member by a vitrified bond. The heater includes a metal rod, a coaxial ceramic tube on the rod, and a coaxial resistance heating coil on one end of the ceramic tube with one end of the coil connected to the rod. The other end of the heating coil is connected to an outer metal conductor crimped around the outside of the ceramic tube. The outer conductor has a portion extending axially along the rod from the heating coil to the other end of the ceramic tube where it provides a second coaxial termination for the heater. A substantial circumferential area of the ceramic tube is presented for vitreous bonding to its supporting electrode terminal.

BRIEF DESCRIPTION OF THE DRAWING

Other objects, features and advantages of the invention will become more apparent from the following description of the preferred embodiments thereof and from the drawing, in which.

DESCRIPTION OF THE PREFERRED EMBODIMENTS

Figure 1:
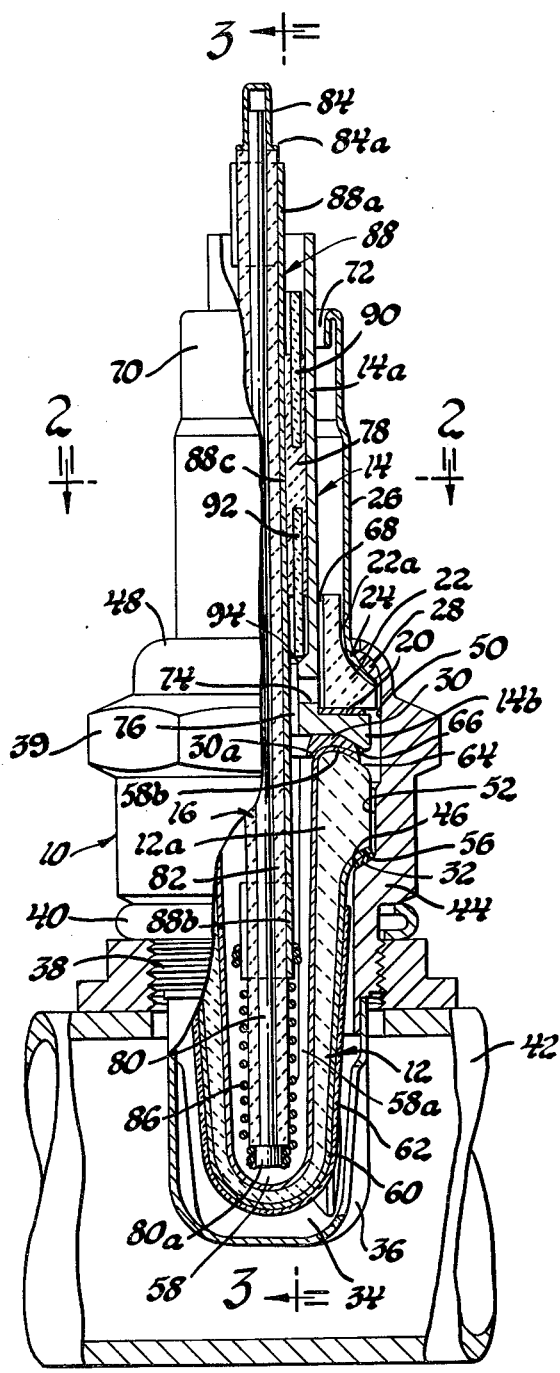
FIG. 1 shows an elevational view in partial longitudinal section of a heated oxygen sensor made in accordance with this invention.
Figure 2:
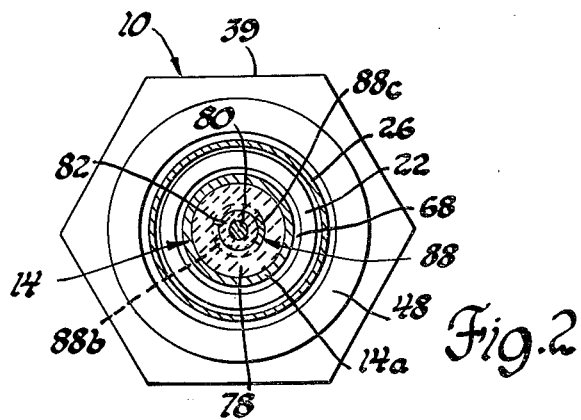
FIG. 2 shows a sectional view along the line 2—2 of FIG. 1.

Reference is now made to the drawing herein which shows a heated galvanic solid electrolyte oxygen sensor having a tubular metal shell 10, a solid electrolyte tube 12 that is closed at its bottom end, an electrode terminal member 14 and a heater 16. The electrolyte tube can be of stabilized zirconia, thoria or the like. However, partially stabilized zirconia may provide enhanced thermal shock resistance. Electrode terminal member 14 has a central tubular portion 14a and a circumferential flange 14b at its lower end. Heater 16 is coaxially supported within terminal tube 14a and forms a subassembly therewith in which heater 16 is electrically isolated from terminal member 14. The subassembly is specifically illustrated in FIG. 3, and will hereinafter be described in further detail.

A flat mica washer 20 is disposed on the upper surface of flange 14b. A ceramic ring 22 is concentrically disposed on mica washer 20 around terminal tube 14a. It has an outer surface 22a with an upwardly decreasing taper. A flared lower end 24 of a tubular upper metal shield 26 nests on the tapered outer surface 22a of ceramic ring 22. An annular metal gasket 28 surrounds the flared lower end 24 of shield 26. Below terminal flange 14b is an upper metal sealing ring 30, a circumferential flange 12a around the open upper end of the electrolyte tube 12, and a metal lower sealing ring 32. The cup-shaped lower metal shield 34 is affixed to the lower end of shell 10 surrounding the otherwise exposed lower end of electrolyte tube 12. Lower metal shield 34 has louvers 36 for entry of exhaust gases. All of the aforementioned elements are coaxially aligned. The sealing rings 30 and 32 can be of any soft metal, such as copper or nickel. The shell 10 and metal shield 26 and 34 are made of a metal which will withstand the conditions of sensor use, as for example stainless steel and nickel based alloys. Ceramic ring 22 can be of any suitable ceramic such as for example alumina. Annular metal gasekt 28 can be of soft steel.

On its outer surface, tubular metal shell 10 has circumferential threads 38 for mounting the sensor in an automobile exhaust pipe 42. Above threads 38 is an outer annular soft seal gasket 40. Above gasket 40 is a circumferential hexagonal array of surface flats 39, for tightening shell 10 in an exhaust pipe 42. If desired, the sensor could be alternately mounted in an exhaust system manifold, tailpipe or special parallel exhaust passage. On its inner surface, shell 10 has a lower inward circumferential flange 44, providing an annular sloped shoulder 46. Shoulder 46 forms a tapered seat on which lower sealing ring 32 is disposed. The upper end of shell 10 has an inward circumferential flange 48, formed by crimping or rolling over the soft steel gasket 28. Sloped shoulder 46 and upper flange 48 cooperate to concentrically clamp the aforementioned flanges, rings and washers within shell 10 in a predetermined fixed coaxial relationship.

The inner surface of shell 10 is generally cylindrical. Above shoulder 46 it has a larger diameter portion 50 and a smaller diameter portion 52. Portion 50 is of larger diameter to radially space shell 10 from the outer periphery of electrode terminal flange 14b for electrical isolation purposes. Portion 52 is of a diameter only slightly larger than the outer diameter of the adjacent electrolyte tube flange 12a. The adjacent tube and shell diameters are sufficiently close to provide substantial coaxial alignment but not so close as to prevent easy assembly. About 0.040 inch or less nominal different may be suitable.

Solid electrolyte tube 12 is tapered from its upper end to its closed lower end. The upper end has a larger diameter portion that forms circumferential circular concentric flange 12a. Wall thickness or the electrolyte tube 12 gradually decreases from flange 12a to the tube lower end. Flange 12a has a lower surface 56 which forms a sloped shoulder generally similar in slope to the shoulder 46 of shell 10. Shoulders 46 and 56 cooperate, along with the shell reduced diameter portion 52, to coaxially align electrolyte tube 12 within shell 10. Lower metal sealing ring 32, between shoulders 46 and 56, provides a gas tight seal, and low resistance electrical communication between the surfaces.

A first porous thick film platinum electrode 58 fully covers the bottom inner surface of electrolyte tube 12. This inner electrode 58 serves as a reference electrode. In this case an air electrode for the sensor. A conductive strip-like coating 58a extends up the tube inner surface from electrode 58 to the open end of the tube 12, where it intersects with the conductive coating 58b on the end face of the electrolyte tube 12. Conductive coating 58b can merely be a stripe across the end face of the electrolyte tube or be a continuous circumferential coating. The platinum electrode 58 and conductive coating 58a and 58b can be a continuous layer formed by brushing on a platinum paste and then firing it, as is usual.

A second porous thick film platinum electrode 60 covers the entire outer surface of tube 12, including the shoulder 56, below flange 12a. This outer electrode 60 serves as the exhaust gas electrode for the sensor. Outer platinum electrode 60 can be formed in the same manner as described above for inner electrode 58. However, it may be more desirable to apply it by evaporation, chemical vapor depoisiton, sputtering, or other such techniques. Outer electrode 60 is in low resistance electrical contact with shell 10 through the lower soft metal gasket 32. Hence, this electrode is also in low resistance electrical communication with upper shield 26 and exhaust pipe 42. A porous ceramic coating 62 of alumina, spinel, or the like, preferably covers the outer electrode 60 below electrolyte tube shoulder 56.

The upper end of electrolyte tube 12 is chamfered on its periphery, forming a sloped shoulder 64. The outer periphery of sealing ring 30 has a complementary contour. The inner periphery of the sealing ring has an axial flange 30a to facilitate concentric seating of sealing ring 30 on the open end face of tube 12. Inner electrode 58 and electrode terminal 14 are in low resistance electrical contact through platinum strip 58a, conductive coating 58b and sealing ring 30. Electrode terminal flange 14b has a sloped shoulder 66 on the outer periphery of its lower face, at least generally corresponding to sealing ring 30 and electrolyte tube shoulder 64. Sloped shoulders 64 and 66 cooperate to coaxially align electrode terminal 14 with electrolyte tube 12.

The upper surface of flange 14b is normal to the axis of terminal tube 14a. Also the lower end face of ceramic ring 22 is normal to the longitudinal axis of coaxial passage 68 extending through the ceramic ring. The tapered outer surface 22a of ceramic ring 22 coacts with the adjacent metal gasket 28 and shell flange 48 to not only clamp the components together but also coaxially align ceramic ring 22 and its passage 68 within the shell 10. Passage 68 has a diameter of 0.040 inch, preferably about 0.705 −0.01 inch larger than the outer diameter of terminal tube 14a, enhancing axial alignment of terminal 14 and the subassembly of which it is a part. As can be seen, the taper 22a on the ceramic ring 22 is gradual at its upper end to enhance coaxial alignment and more abrupt at its lower end to enhance the clamping effect. Since flared lower end 24 of upper metal shield 26 conforms to the taper 22a of the ceramic ring and nests thereon under gasket 28, shield 26 is also coaxially aligned.

The upper end of shield 26 is open and radially spaced from heater 16. Shield 26 is therefore electrically isolated from heater 16. While not shown, shield 26 can have a conformation above ceramic ring 22 to retain an upper insulating spacer in place and help retain a terminal connector that may be attached. As mentioned, shield 26 is at a low resistance of electrical communication with the outer 60 on the electrolyte tube 12. Shield 26 can, therefore, serve as a ground connection, if desired, instead of exhaust pipe 42. To insure low resistance connection, an electroplated coating (not shown) of silver or the like can be provided on the upper end 70 of shield 26.

The open upper end of shield 26 provides an aperture 72 through which ambient air can enter the interior of the sensor. Air entering the sensor through aperture 72 passes down through shield 26 to the narrow generally annular passage 68 between the ceramic ring 22 and electrode terminal tubular portion 14a. Air entering annular passage 68 passes downwardly to aperture 74 in the lower wall of tube 14a, and through aperture 74 to a lower narrow generally annular passage 76 between heater 16 and the lower end of terminal tube 14a. A spacing of about 0.005 -0.01 inch between the inner diameter of tube 14a and the outer diameter of heater 16 is adequate to provide the lower annular passage 76. Air passes through passage 76 into the interior of electrolyte tube 12, where it contacts the inner electrode 58. Thus, the interior of the electrolyte tube 12 communicates with outside air to a baffle passage. Thus, the electrolyte tube interior and the lower end of heater 16 are protected from particulate contaminants, water splash, etc. It should also be mentioned that passages 68 and 76 are formed by merely appropriately dimensioning respective parts with a generous manufacturing clearance. No intricate machining is required and assembly is simple. Hence, passage 68 of ceramic ring 22 is in coaxial alignment of the heater-terminal subassembly. Passage 68 can be quite narrow, since only a very small rate of air flow is necessary during sensor operation. The rate of air flow resulting from air leakage to only normal manufacturing tolerances, e.g., 0.003–0.005 inch minimum clearance may be all that is necessary to provide air flow path.

Figure 3:
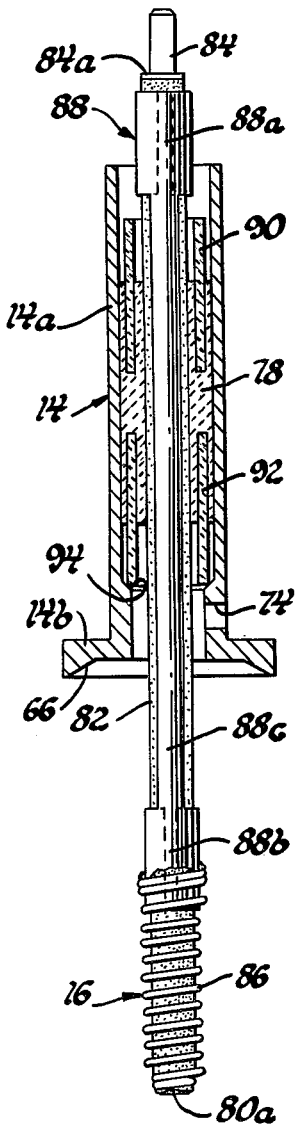
FIG. 3 shows a sectional view along the line 3—3 of FIG. 1.

As can be seen better by also referring to FIG. 3, heater 16 is coaxially bonded within electrode terminal tube 14a by a fused glass 78. By fused glass we mean a body of glass that has been melted and resolidified in place whereby the resolidified glass body adheres to surfaces it contacts. Heater 16 includes a center rod 80 having a circumferential flange 80a at its lower end which provides an upwardly disposed facing circumferential shoulder. Rod 80 is coaxially disposed within a cylindrical ceramic tube of alumina, magnesia, beryllia, or the like. The lower end of ceramic tube 82 abuts the upwardly facing shoulder on rod flange 80a. The other end of rod 80 is displaced axially outwardly from the upper end of ceramic tube 82. An end cap 84 on this end of rod 80 has a flange 84a that abuts the adjacent upper end of ceramic tube 82 to lock rod 80 within ceramic tube 82. End cap 84 can be affixed to the end of rod 80 in any convenient manner, as for example by crimping, soldering, welding, etc. If desired, end cap 84 can be silver plated (not shown) to insure making a low resistance terminal connection thereon. A resistance heating coil 86 is coaxially disposed on the lower end of ceramic tube 82. Heating coil 86 can be a nichrome wire helically wound around the ceramic tube 82, with individual turns of the coil axially spaced to prevent electrical shorting. The lower end of coil 86 has smaller diameter turns around rod flange 80a. These turns are welded to flange 80a to support the coil and provide electrical connection to rod 80, which can then serve as an inner coaxial heater terminal.

A discrete metal conductor 88 is crimped around the outer surface of ceramic tube 82. It has three portions, the first of which is an upper portion 88a crimped around the upper end of ceramic tube 82. It has a lower portion 88b of conductor 88 which is axially spaced down from the upper portion 88a, where it is crimped around the lower end of ceramic tube 82. A strip-like portion 88c on conductor 88 connects upper and lower portions 88a and 88b. Lower portion 88b is crimped around ceramic tube 82 adjacent the upper end of resistance heating coil 86. Upper turns of coil 86 are directly on portion 88b and welded to it. Through the interconnecting strip 88b, upper portion 88a provides an outer coaxial terminal for the coil 86.

It can be seen that the intermediate portion 88c of conductor 88 extends completely through the area of fused glass along ceramic tube 82. Portion 88c thus interconnects portions 88a and 88b, yet leaves a major circumferential proportion of ceramic conductor tube 82 exposed to the fused glass 78. Fused glass 78 is, therefore, directly in contact with the ceramic tube for enhanced bonding. No knurling or other special treatments of the strip portion 88c need be performed to insure good heater bonding to, and support within, electrode terminal tube 14a. It should be recognized that both portions 88a and 88b could be axially enlarged and still provide a significant circumferential exposure of ceramic tube 82 in the area of the fused glass 78. However, this is not particularly preferred since it would add to cost and no significant benefits are expected. In most instances, it is preferred that about 5–10 mm of tube length be exposed to fused glass 78. Also, the longer the length exposed to the fused glass, the less tube circumference need be exposed. However, in most instances we prefer at least three-quarters of tube circumference be directly exposed to the fused glass whether conductor middle portion 88c is linear or a helix.

Rod 80 is preferably clamped in place so that it is not only axially immovable on ceramic tube 82 but also not rotatable within it. It is expected that the construction described will adequately lock rod 80 in place. However, if not, mechanical interlocks can be provided. As for example, the ends of the ceramic tube 82 can be notched and flanges 80a and 84a have mating bosses that interlock with their adjacent notches to prevent relative rotation between rod 80 and ceramic tube 82. Analogously, the ends of rod 80 could alternatively be crimped to provide interlock embossments. Such embossments would not only radially but axially lock rod 80 on ceramic tube 82.

Portions 88a and 88b of outer conductor 88 should be crimped substantially entirely around ceramic tube 82 for best results. In each instance upper portion 88a will provide a highly satisfactory coaxial terminal. Analogously, lower portion 88b will provide a highly rigid connection to resistance heating coil 86. With coil 86 welded to both the crimped connector 88 and the rigid center rod, it is well supported. In some applications, it may be satisfactory to prewind coil 86 as a discrete helix before assembly on tube 82. One then would simply slide it onto the lower portion 88b of the outer connector and flange 80a of the inner connector for welding. In other applications, a somewhat closer fit may be desired between the rod 82 and coil 86. In such instance, it may be more desirable to wind coil 86 in place on rod 82 as well as over the connector portions 88b and 80a. In still other applications, it may even be desirable to provide a helical groove for coil 86 in the outer surface of ceramic tube 82 as shown in U.S. Pat. No. 3,546,085 Sayles. Tube 82 could even be provided with embossments to interlock with portions of crimped conductor 88. However, these latter alternatives add to manufacturing and assembly costs, and probably are unnecessary except for the most rigorous applications. In some applications, it may be desirable that metal member 88 be crimped to ceramic tube 82 in only one location rather than two as described herein. For example, it may be desirable only to crimp member 88 in a lower region such as portion 88b or in an upper region, such as portion 88a. It is doubtful that it would be desirable for conductor 88 to only include a single crimped portion 88a or 88b without also including an integral extension such as portion 88c, respectively to coil 86 or to the upper end of tube 82. A thick film printed conductor could be substituted for portion 88c and for upper portion 88a. However, this is not desirable.

Above and below fused glass 78 heater 16 is respectively spaced from electrode terminal tubular portion 14a by an upper ceramic sleeve 90 and a lower ceramic sleeve 92. As can be seen lower ceramic sleeve 92 is supported on a circumferential shoulder 94 on the inner surface of terminal tubular portion 14a. Ceramic sleeves 90 and 92 radially space heater 16 from the inner surface of electrode terminal tube 14a along its entire length. This not only coaxially aligns the heater in tube 14a but also thermally separates heater 16 and terminal tube 14a and electrically isolates them. It should also be recognized that a substantial portion of the outer surface of heater 16 is thermally non-conductive. Only outer conductor 88 is heat conductive. Thus, less heat is lost by upward conduction through the heater during heating. Of course, the sensor can be continuously heated during sensing, since it is electrically isolated from sensor terminals. It should also be mentioned that the coaxial inner and outer heater terminals 84 and 88a and outer surface on the adjacent outer end of terminal tube 14a can be electroplated with silver (not shown) to enhance low resistance terminal connections thereat.

Fused glass 78 initially was a cylindrical body slightly longer than the space between ceramic sleeves 90 and 92 shown in the drawing. The glass cylinder in sleeves 90 and 92 were assembled in tube 14a, with sleeve 90 projecting slightly beyond the upper end of terminal tube portion 14a. Heater 16 was coaxially disposed within them in proper axial displacement with respect to the ends of tube 14a. The subassembly was then heated, the glass cylinder melted, and the upper ceramic sleeve 90 moved further into tube 14a to the position shown in the drawing. As a result, the molten glass completely filled an annular region between ceramic tube 82 and the radially adjacent terminal tubular portion 14a in the area of facing end surfaces on ceramic sleeves 90 and 92. Concurrently, portions of the molten glass also were actually displaced a short distance along the inner and outer surfaces of the adjacent ends on ceramic sleeves 90 and 92. Along this distance the molten glass filled the space between the sleeves and the heater and between the sleeves and tube 14a. The assembly was then cooled. The glass solidified and bonded to the heater 16, terminal tubular portion 14a and ceramic sleeves 90 and 92. The glass bonded strongly to a major circumferential surface of ceramic tube 82 and to the outer conductor strip portion 88c. The glass not only supports the heater within the terminal portion 14a but also provides a seal. The glass composition is not critical. Any glass can be used if meltable at a temperature above the highest operating temperature expected for the sensor, usually above 700° C., and below a temperature deleteriously affecting the heater or terminal materials such as their melting or sintering temperatures. A glass melting at about 1000° C. can be used.

Tube 14a is normal to the upper surface of flange 14b. For best results, tube portion 14a is generally about 15 times longer, preferably about 10 to 15 times or more longer than the dimension of its inner diameter. Since tube 14a has considerable length, ceramic sleeves 90 and 92 can be made somewhat loosely fitting within tube 14a to ease assembly. Nonetheless, they can effectively, precisely align heater 16 within the tube 14b. However, even if somewhat loosely fitting, sleeves 90 and 92 are rigidly held in place by the fused glass 78 in the finished subassembly shown in FIG. 3 of the drawings. Thus, the axis of heater 16 is maintained substantially normal to the upper surface of electrode terminal flange 14b.

The embodiments of the invention in which an exclusive property or privilege is claimed are defined as follows:

1. In a coaxial cylindrical galvanic exhaust gas oxygen sensor have a metal shell, an electrolyte member, an electrode terminal tube and a heater, and the heater is supported in a subassembly with the electrode terminal by a fused glass bond, the improvement wherein the heater comprises a ceramic tube having two open ends, a resistance heating coil wound around one tube end and directly exposed to said electrolyte member, a metal rod coaxially fixed in the tube with its ends and outwardly displaced from tube ends, one rod end electrically connected to an end of said coil and the other rod end providing an inner coaxial terminal for said heating coil, and a metal member crimped around the outside of said ceramic tube and electrically connected to an opposite end of said heating coil but leaving a major proportion of said ceramic tube circumference exposed, whereby electrolyte member heating efficiency is increased, subassembly costs are reduced, and electrode terminal bonding is enhanced.

2. In a coaxial cylindrical galvanic exhaust gas oxygen sensor having a metal shell, an electrolyte member, an electrode terminal tube and a heater, and the heater is supported in a subassembly with the electrode terminal by a fused glass bond, the improvement wherein the heater comprises a ceramic tube having two open ends, a resistance heating coil wound around one tube end and directly exposed to said electrolyte member, a metal rod coaxially fixed in the tube with its ends and outwardly displaced from tube ends, one rod end electrically connected to an end of said coil and the other rod end providing an inner coaxial terminal for said heating coil, and a metal member crimped around the outside of said ceramic tube, said metal member having a first portion adjacent said other rod end, an axially spaced second portion electrically connected to an opposite end of said heating coil, and a strip-like third portion interconnecting the first two portions but leaving a major proportion of said ceramic tube circumference exposed, whereby the fused glass is bonded directly to said exposed ceramic tube for rigidly locking said heater in subassembly with said electrode terminal.

3. In a cylindrical galvanic exhaust gas oxygen sensor coaxially having a tubular metal shell, a tubular electrolyte member, an electrode terminal tube and a heater, and the heater is supported in coaxial subassembly with the terminal tube by a fused glass bond, the improvement wherein the heater comprises a ceramic tube having two open ends, a resistance heating coil wound around one tube end and directly exposed to said electrolyte member, a metal rod coaxially disposed in the tube with its ends outwardly displaced from tube ends, means for at least axially locking the rod in the tube, one rod end being welded to an end of said coil and the other rod end providing an inner coaxial terminal for said heating coil, and a discrete outer metal member having two axially spaced portions crimped around said tube and an interconnecting strip-like third portion, the first portion being adjacent said other rod end and providing an outer coaxial terminal for said heating coil, the second portion being welded to said heating coil, and the interconnecting third portion leaving a significant length and substantial circumference of said ceramic tube exposed, and the fused glass in the heater-electrode terminal subassembly is bonded directly to the so exposed ceramic rod and interconnecting portion to rigidly lock the heater in subassembly with the electrode terminal.

* * * * *